United States Patent
Nye

(10) Patent No.: US 7,421,367 B2
(45) Date of Patent: Sep. 2, 2008

(54) HANDHELD COMPUTING DEVICE FOR PERFORMING MULTITASKS IN HEALTHCARE APPLICATIONS

(76) Inventor: Pamela F. Nye, 419 Beasley Dr., Apt. T-1, Greenville, NC (US) 27834-2878

( * ) Notice: Subject to any disclaimer, the term of this patent is extended or adjusted under 35 U.S.C. 154(b) by 199 days.

(21) Appl. No.: 11/018,118

(22) Filed: Dec. 21, 2004

(65) Prior Publication Data

US 2006/0136167 A1 Jun. 22, 2006

(51) Int. Cl.
*G06F 15/00* (2006.01)
(52) U.S. Cl. ............. 702/127; 705/28; 340/539.26; 340/539.29
(58) Field of Classification Search ......... 702/127–131, 702/133, 135, 136, 138–140, 3, 176, 187; 340/539.26, 539.29
See application file for complete search history.

(56) References Cited

U.S. PATENT DOCUMENTS

| | | | | |
|---|---|---|---|---|
| 4,698,505 A | * | 10/1987 | Brand | 250/337 |
| 4,835,372 A | * | 5/1989 | Gombrich et al. | 235/375 |
| 4,943,939 A | * | 7/1990 | Hoover | 702/128 |
| 5,142,930 A | * | 9/1992 | Allen et al. | 74/469 |
| 5,409,511 A | * | 4/1995 | Paul | 96/408 |
| 5,456,702 A | * | 10/1995 | Falk | 607/105 |
| 5,483,826 A | * | 1/1996 | Schultz et al. | 73/146.5 |
| 5,830,058 A | * | 11/1998 | Rosjo | 454/187 |
| 5,912,818 A | * | 6/1999 | McGrady et al. | 700/232 |
| 6,057,758 A | * | 5/2000 | Dempsey et al. | 340/539.12 |
| 6,111,509 A | * | 8/2000 | Holmes | 340/573.4 |
| 2002/0049650 A1 | * | 4/2002 | Reff | 705/29 |
| 2002/0193076 A1 | * | 12/2002 | Rogers et al. | 455/66 |
| 2004/0010425 A1 | * | 1/2004 | Wilkes et al. | 705/3 |
| 2004/0236547 A1 | * | 11/2004 | Rappaport et al. | 703/2 |
| 2005/0091431 A1 | * | 4/2005 | Olodort et al. | 710/72 |
| 2005/0134568 A1 | * | 6/2005 | Hill et al. | 345/169 |

* cited by examiner

*Primary Examiner*—Manuel L Barbee
(74) *Attorney, Agent, or Firm*—Coats & Bennett, P.L.L.C

(57) ABSTRACT

A handheld computing device for use in hospitals, operating rooms, and other medical care facilities. The handheld computing device includes a processor, display, user interface, memory, one or more embedded environmental sensors, and one or more scanners for reading identifier codes that uniquely identify sterile and non-sterile supplies, instruments and disposable components thereof and other inventory items and supplies that are used in the course of a medical procedure such as surgery. To manage the accounting of various items used in an operating room for example, the handheld computing device is provided with an RF tag reader and a barcode reader to read and identify medical items that are used in the course of a medical procedure. In the course of scanning such identifier codes, the handheld computing device receives inventory accounting information that is stored within the memory of the device, and which can be subsequently downloaded and transferred to one or more external databases. Further, in one embodiment, the environmental sensors may include temperature, humidity and pressure sensors that sense, record and store temperature, humidity and pressure data.

33 Claims, 7 Drawing Sheets

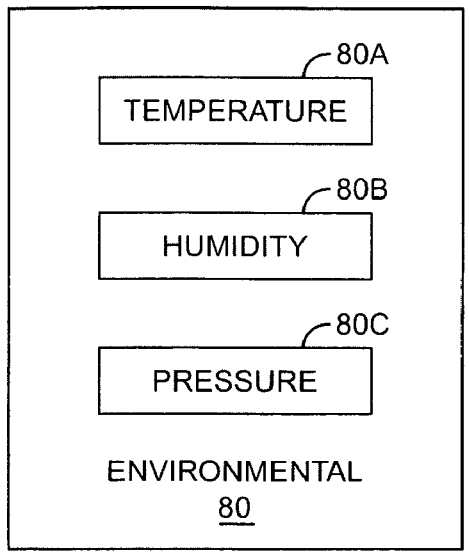
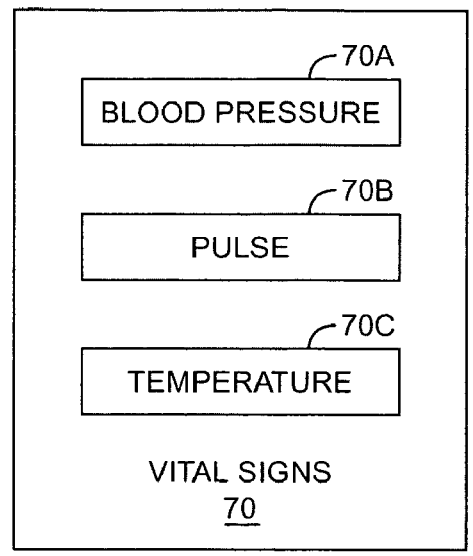
FIG. 9
FIG. 10
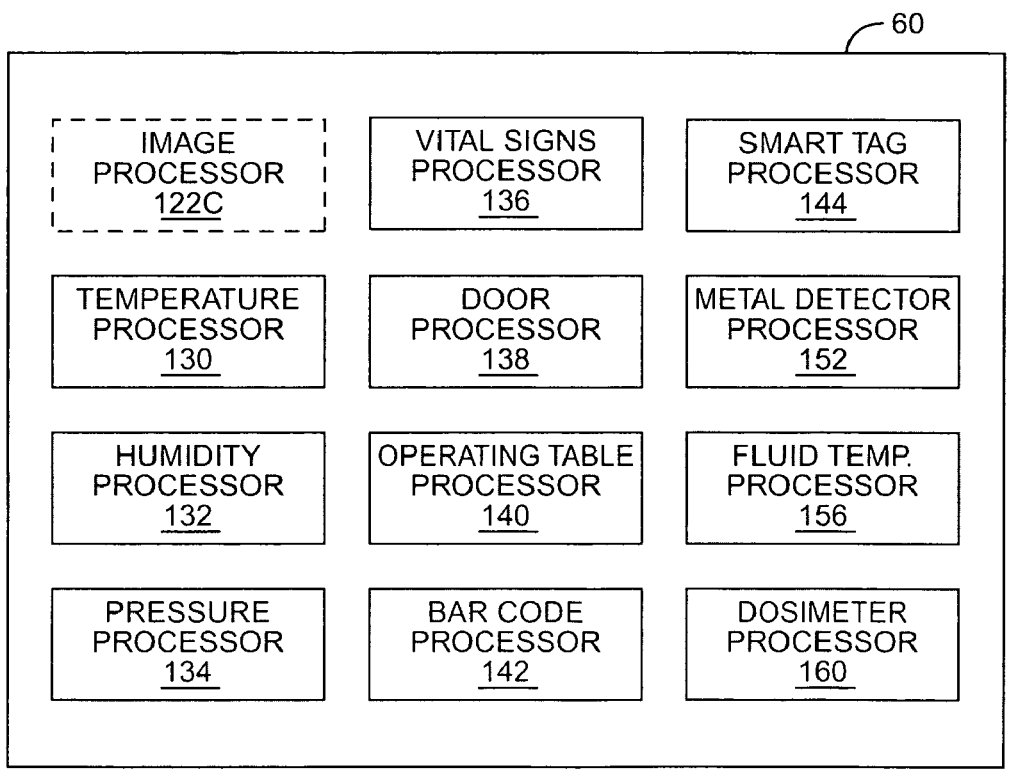
FIG. 11

HANDHELD COMPUTING DEVICE FOR PERFORMING MULTITASKS IN HEALTHCARE APPLICATIONS

FIELD OF THE INVENTION

The present invention relates to handheld computing devices and more particularly to a handheld computing device designed to perform multitasks in a wide range of healthcare applications.

BACKGROUND OF THE INVENTION

In recent years hospitals and medical care facilities in general have committed tremendous resources to upgrading information technology systems. There is, of course, an underlying problem that encourages this automation. Medical errors and the inability to consistently and accurately count for and track costs are serious problems facing the medical community as a whole. While there is a clear need to continue to improve information management in hospitals and healthcare facilities, it is not so clear how best to accomplish such. There are many challenges that face hospitals and medical care facilities when it comes to designing and implementing effective and efficient information technology systems. After all, information technology systems designed for hospitals and medical care facilities must be designed around physicians, nurses and other medical staff that are almost always in constant motion. Care must be given to providing information technology systems that do not disrupt the process of care provided by these institutions.

Generally, information technology systems presently utilized in hospitals and medical care facilities rely substantially on fixed centralized stations. However, this approach does not adequately address the problems of medical errors and delays in processing and managing clinical information. In the end, centralized fixed stations alone do not lend themselves to convenience and efficiency. A computer in every hospital room, for example, is probably not the best solution. Such an approach is very expensive and does not lend itself to the natural process of healthcare that takes place in a hospital or medical care facility. Placing information technology systems, including handheld computing devices, in the hands of the medical staff can result in increased productivity, a decrease in errors, and a reduced documentation workload for nurses that are already in short supply.

Another serious problem for hospitals and medical care facilities is cost accounting, and particularly tracking costs, managing and controlling inventory, and billing all costs to the appropriate patient. Hospitals and healthcare facilities typically maintain large inventories that must be managed and controlled. Huge numbers of items are transferred in and transferred out central supply and operating rooms on a daily basis. Those in charge of inventory control must take steps to discern what supplies are being used, the timeframe that they are being used, who they are being used for, and how often the supplies or items are called for. An efficient and accurate inventory management and control system will account for all items used.

For the most part, inventory management control systems utilized in healthcare facilities are less sophisticated than one finds in other industries. Items are often ordered as needed or when certain items become critically low.

In some cases, when an item is used during an operation, a nurse or attendant will fetch the item from a central inventory room and may make an appropriate paper entry. In many cases there is minimum accountability as to the items that have been removed from the central supply. In general, for the most part, in hospitals and other healthcare facilities, the methods and procedures for maintaining and controlling inventory is replete with errors and omissions.

The task of accurately tracking costs in an operating room, for example, is a difficult undertaking especially when viewed in the context that when surgeries are performed, that the care and well being of the patient comes first and all other matters, including cost accounting, are secondary. During the course of a surgery various items and supplies are used for the patient's benefits and all of these should be accounted for. For example, basic sterile supplies, sometimes referred to as sterile bundles that include sterile gowns, gloves, bowls, etc., will be used. Further, trays of instruments and disposable components associated with these instruments will be used. In addition, during the course of a surgery, various instrumentation will be utilized and some of the instrumentation will include disposable components. Further, there are other disposable items such as staples, staplers, etc. In many cases implants are utilized. This is simply a sample of the types of items and objects that are either spent or used during the course of a surgery. In practice, many hospitals utilize hand accounting to track these items of cost and to record them to the patient's account. As a result, the documentation of items used during surgical procedures is often incomplete or not available. Typically there are no graphical images of any instruments or items utilized in a surgery which could provide proof of use in cases where billing records are questioned. Importantly, many items are used, but go unaccounted for. These losses that are experienced by virtually every hospital that operates operating rooms are huge and continue to play an important part in the seemingly uncontrollable escalation of healthcare costs.

SUMMARY OF THE INVENTION

The present invention is a handheld computing device that is particularly adapted for use in hospitals, operating rooms, and other medical care facilities. The handheld computing device is capable of performing a wide range of functions within a medical facility ranging from cost accounting and managing and controlling inventory to sensing and recording in real time environmental and other relevant conditions in an operating room. Additionally, the handheld computing device has applications in other medical areas such as telemedicine and facilitating the access to medical libraries and medical information throughout the world.

In one particular embodiment of the present invention, a handheld computing device is provided that includes a processor, a memory, and a display. In addition, the handheld computing device includes on or more embedded environmental sensors, such as a temperature sensor, a humidity sensor and a pressure sensor, that enables the handheld computing device to sense, analyze, process and store the environmental conditions in the memory of the device.

In another embodiment of the present invention, the handheld computing device is provided with an inventory management module that includes scanning devices, such as a barcode scanner or an RF tag reader, that function to read unique identifiers associated with items such as supplies, instruments and disposable items used during the course of a medical procedure.

Further, the present invention entails a method of accounting for items used during a surgical procedure in an operating room. This method entails utilizing the handheld computing device in the operating room to account for items used during the course of a surgery. In particular, the method entails directing a signal from the barcode reader or the RF tag reader toward an identifier that uniquely identifies an item to be used in the surgery. Then, the method entails reading the unique identifier and counting the item identified by the identifier. Next, the method entails storing the count in the handheld computing device and correlating the count with the item counted. Further, the method entails, from time to time, downloading this inventory accounting information from the handheld computer to an external database, such as a main or central database in a hospital.

The present invention provides a simple, user-friendly, highly portable personal handheld computing device that is capable of performing multitasks, especially in a wide range of healthcare applications. Use of the handheld computing device of the present application will promote the development of reliable methods of maintaining accurate accounting records through a system of data collection that emphasizes simplicity. By utilizing the handheld computing device in medical care accounting applications, more accurate records will be generated that reflect the actual cost of medical care and the use of the handheld computing device of the present invention will enable this objective to be carried out in an efficient and cost effective manner.

Other objects and advantages of the present invention will become apparent and obvious from a study of the following description and the accompanying drawings, which are merely illustrative of such invention.

BRIEF DESCRIPTION OF THE DRAWINGS

FIG. 9 is a schematic illustration of a series of environmental sensors that are embedded in the computing device.

FIG. 10 is a schematic illustration of a series of vital sign sensors that may be embedded into the computing device.

FIG. 11 is an expanded illustration of the controller shown in FIG. 6 and illustrates the types of microprocessors that form a part of the controller.

DETAILED DESCRIPTION OF THE INVENTION

Figure 1:
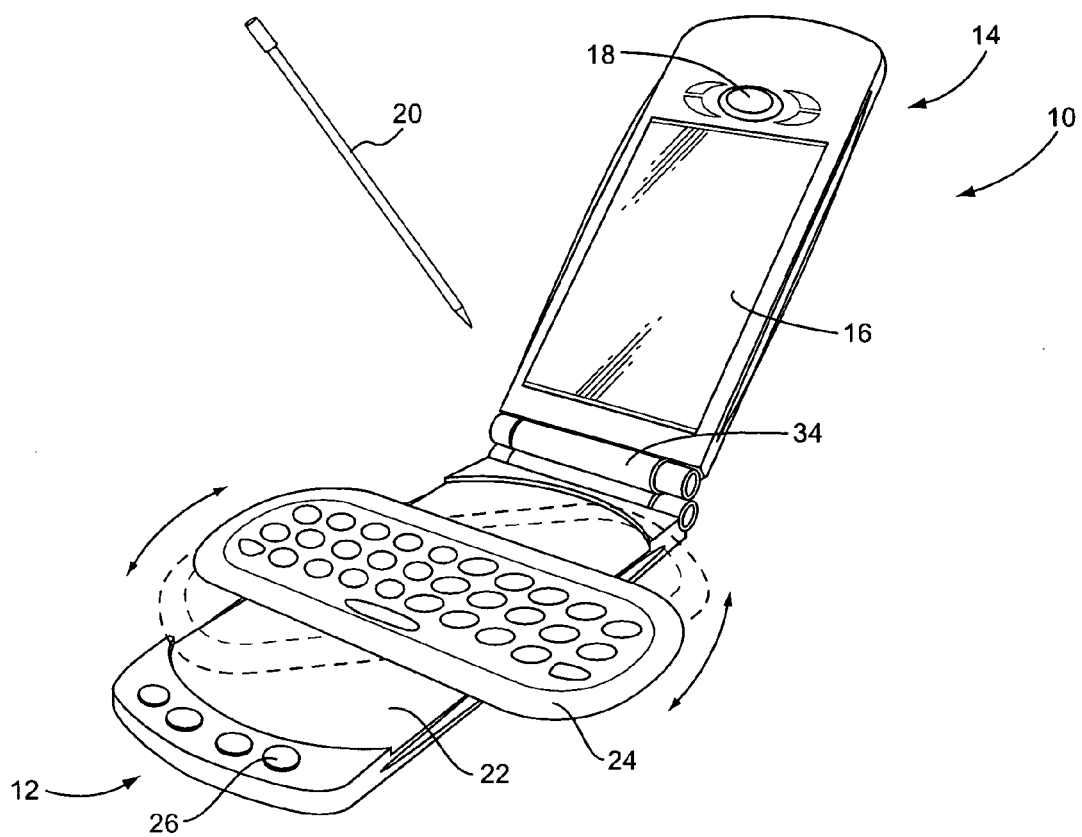
FIG. 1 is a perspective view of the handheld computing device of the present invention shown in the normal open position.
Figure 2:
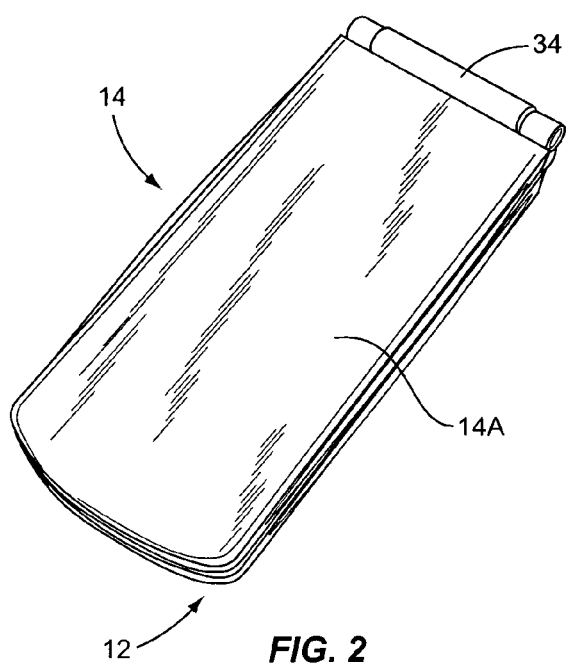
FIG. 2 is a perspective view of the handheld computing device shown in the closed position.

With further reference to the drawings, the handheld computing device 10 is shown therein and indicated generally by the numeral 10. Handheld computing device 10 includes a housing that, in the embodiment illustrated, is of a clamshell type. The housing of the computing device 10 includes a base indicated generally by the numeral 12 and a flip indicated generally by the numeral 14. Flip 14 is pivotally connected to one end portion of the base 12 and can be pivoted between open and closed positions. Flip 14 is shown in the closed position in FIG. 2 and in the normal open position in FIG. 1. Moreover, flip 14 is fully pivotable from the closed position to an extreme open position where the back 14A of the flip lies directly adjacent the back of the base 12. See FIGS. 3–5. As will be discussed subsequently herein, this orientation (extreme open) of the flip 14 with respect to the base 12 is particularly useful when the handheld computing device 10 is being used to scan or read barcodes or RF tag identifiers during an inventory accounting procedure.

Formed in an end portion of the flip 14 is an expansion slot 15. Expansion slot 15 can be utilized to connect to various peripheral components such as, in one case for example, a CF (compact flash) camera 17. In the case of the CF camera 17, it is appreciated that the digital camera functionality is added to the computing device 10. However, as discussed below, the computing device 10 may be provided with its own embedded digital camera. Formed in the flip in the side that normally faces the base 12 is a screen or display 16. In the case of the present design, it is contemplated that the display 16 would be a touch screen, allowing users to input information into the computing device 10 by a stylus 20. Generally, display 16 is utilized to display a graphical user interface and other data and information to the user. In addition, mounted in the flip, adjacent the display 16, is a rocker 18. Various types of rockers or joysticks can be utilized as a navigational tool. As noted above, the computing device 10 is provided with a stylus 20. While the stylus 20 can be housed or connected in various ways to the computing device 10, it is contemplated that in one design the stylus 20 would be held in a receiver associated with the flip 14.

Turning to base 12, it is seen that the base includes a generally flat, slightly indented surface 22. In the case of the design illustrated herein, the surface 22 is slightly depressed or indented downwardly from opposed raised surfaces disposed on opposite end portions of the base 12. A rotatable QWERTY keyboard 24 is secured to the surface 22. Keyboard 24 is rotatable from a stored position shown in FIG. 4 where the keyboard aligns with base 12 and the flip 14, to a transverse position, shown in FIG. 1. When transversely aligned across the surface 22, opposite end portions of the keyboard 24 overhang the edges of the base 12. While the keyboard may be operated in either orientation, it is contemplated that users will find the keyboard 24 particularly easy and convenient to use when the same assumes the transverse orientation. Note also that the opposed ends of the keyboard 24 are generally arcuate shape. This presents the keyboard with a pleasing appearance, and at the same time it is noted that the raised surfaces adjacent opposite ends of the surface 22 are likewise arcuately shaped. Thus, when the keyboard 24 is rotated to the stored and aligned position, the opposed arcuate end portions of the keyboard generally conform in shape to the raised surfaces that lie adjacent the surface 22.

Disposed below keyboard 24 on the outermost raise arcuate panel is a series of function keys 26. The function keys can be utilized to perform various functional tasks normally associated with a computing device. For example, the function keys may include an ON/OFF key, an ENTER key, and any number of other functions.

Figure 3:
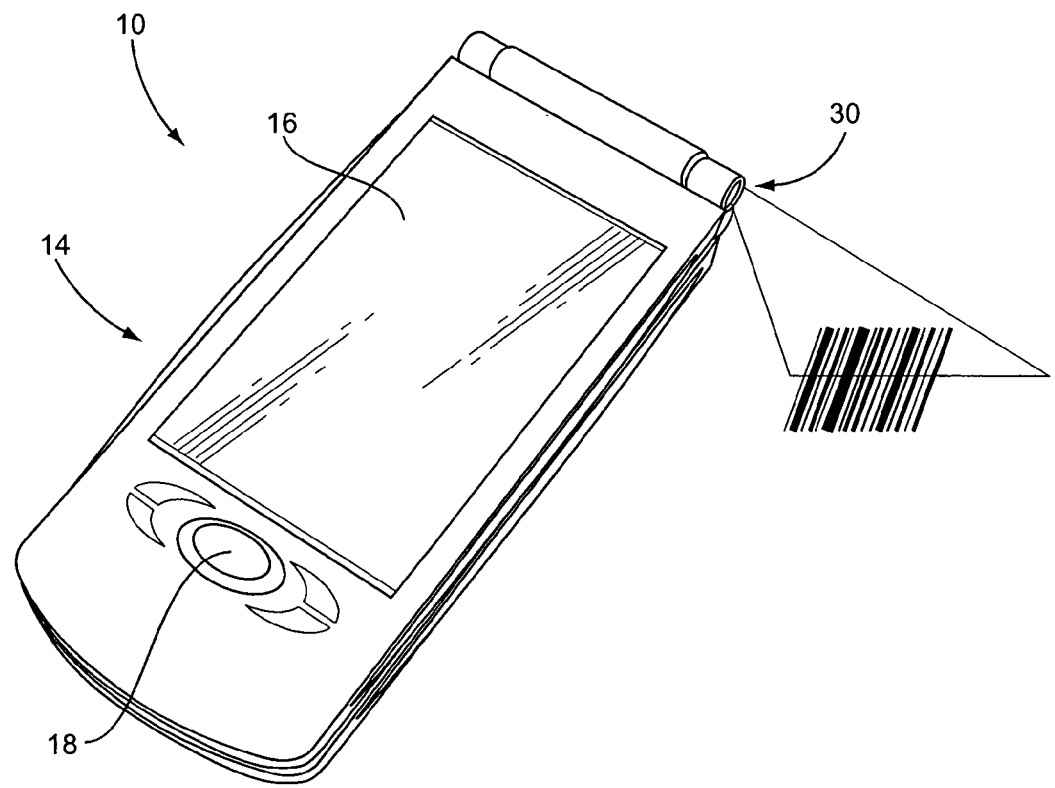
FIG. 3 is a perspective view of the handheld computing device shown in the extreme open position and illustrating the barcode scanner forming a part thereof.
Figure 4:
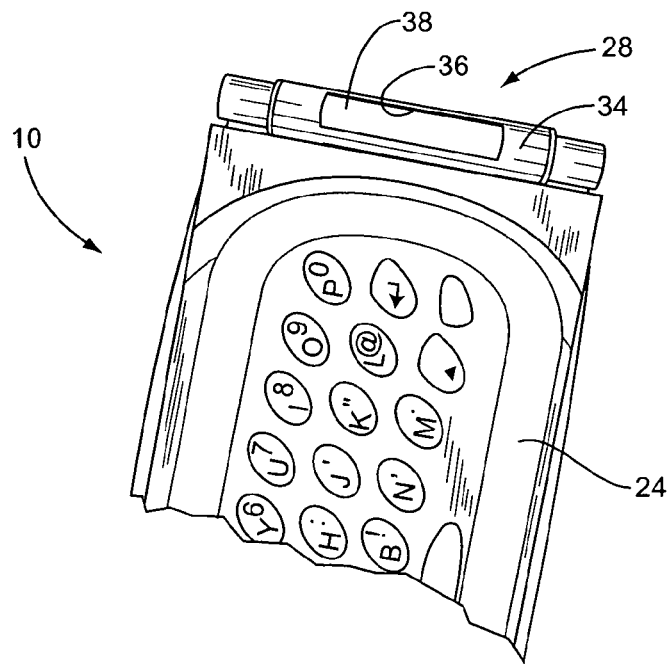
FIG. 4 is a fragmentary view of the handheld computing device illustrating the RF tag reader.
Figure 5:
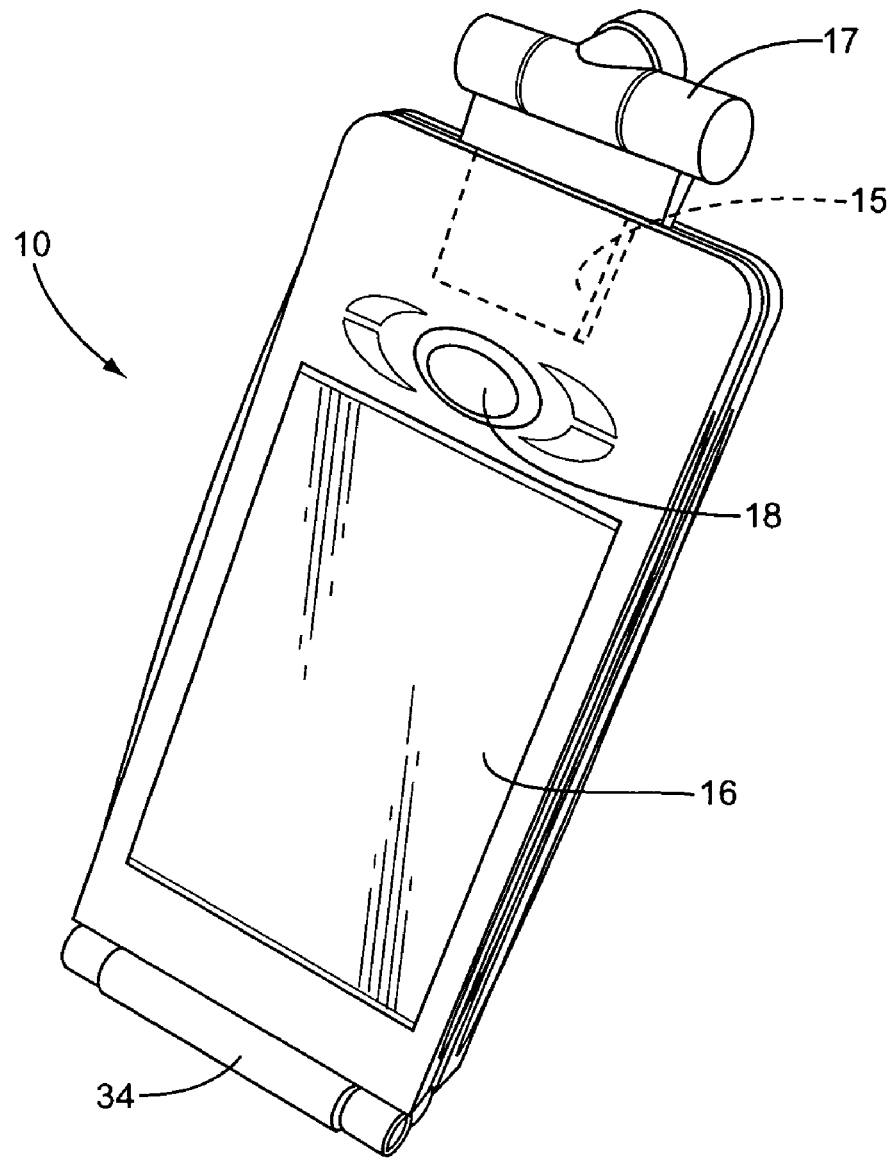
FIG. 5 is a perspective view of the handheld computing device illustrating its expansion slot and the incorporation of a digital camera into the computing device.

Turning to the transverse axis area that lies between the flip 14 and the base 12, as noted above the computing device is provided with one or more pivot pins for connecting the base 12 with the flip 14, but allowing the two basic components to pivotally move with respect to each other. In this axis area, a barcode scanner 28 and RF tag reader 30 is provided. In the case of the present design, a sleeve 34 having an opening 36 extends around a lens 38 that forms a part of the barcode scanner. Sleeve 34 is connected with the flip 14 such that the sleeve 34 is rotated relative to the lens 38 when the flip 14 is rotated from a closed position to an extreme open position where the back 14A thereof lies directly adjacent the back of the base 12. This is illustrated in FIGS. 3 and 4. Otherwise, when the flip 14 assumes the closed position or the normal open position, the sleeve 34 is positioned to cover the lens 38. As noted above, the handheld computing device 10 is provided with an RF tag reading system. In particular, computing unit 10 is provided with an RF tag reader 30. While the RF tag reader 30 can be positioned at various locations in the computing device 10, in the design illustrated herein, a lens associated with the RF tag reader 30 is provided on one side of the pivot axis. This is illustrated in FIG. 3. RF tag reader 30 is operative to direct a signal from the computing device 10 towards an RF tag associated with an item or object.

Figure 6:
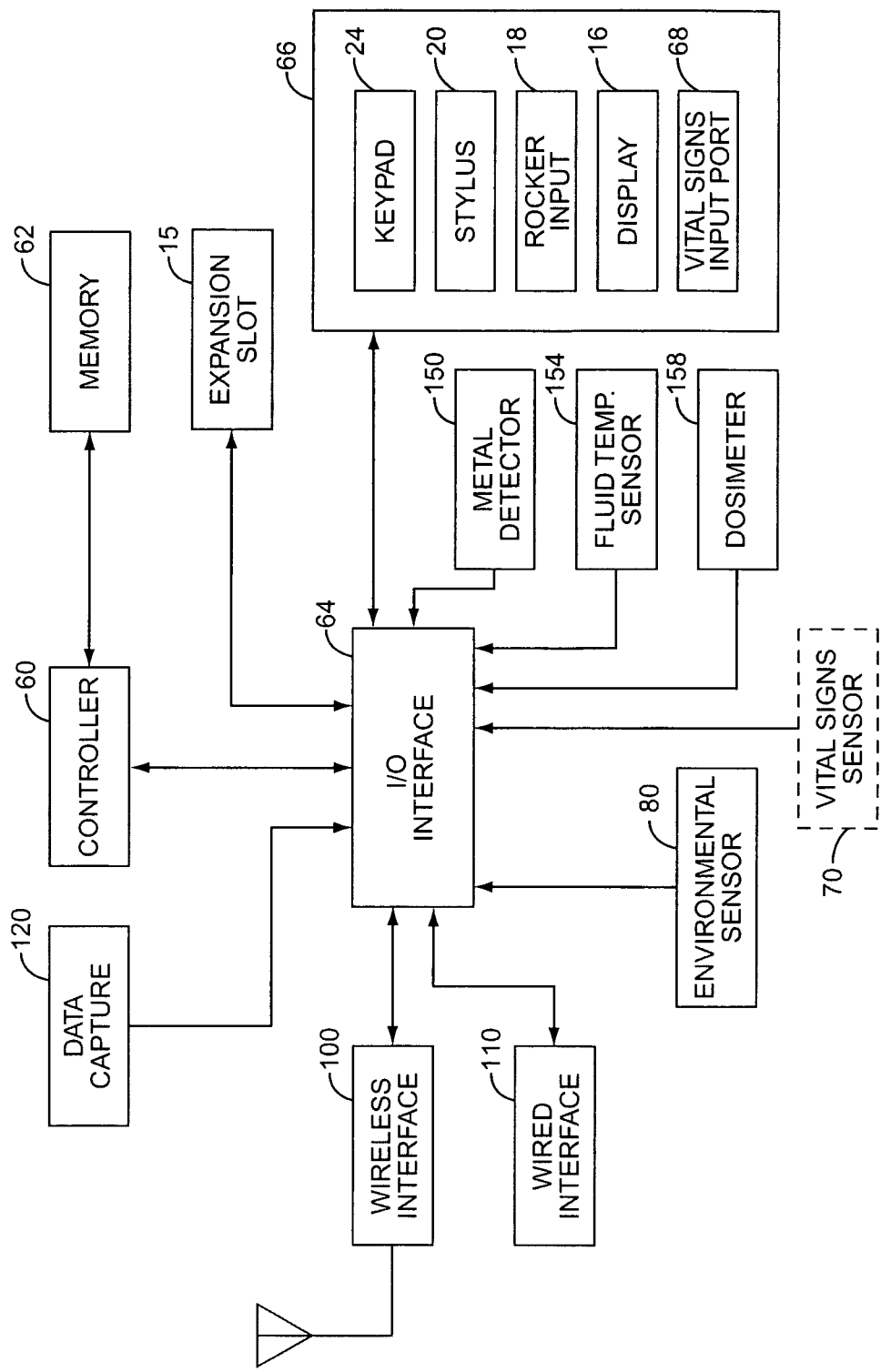
FIG. 6 is a schematic illustration of the basic functional components of the handheld computing device.

The RF tag reader 30 is designed to work in conjunction with a radio frequency tag (not shown) that typically attaches to a package of an item or is somehow associated with an item that would be used in an operating room. Various types of radio frequency tags can be utilized. Typically, an electronic code is written to an electronic memory in the RF tag. The code provides an identification and other data concerning the item associated with the radio frequency tag. In conventional fashion, the data is capable of being discerned by the RF tag reader 30, which in the present disclosure, communicates with the controller 60 (FIG. 6). The RF tag associated with the item to be accounted for is generally a read/write RF tag. The data in each tag is capable of being changed by the RF tag reader 30.

The barcode scanner 28 basically comprises an optical scanning apparatus. In typical cases the barcode scanner emits a laser that is aimed at the barcode, which again is associated with the item to be inventoried or accounted for. A detector typically receives a reflective light signal from the barcode, and wherein the encoded optical pattern in the barcode causes a reflective pattern in the light signal to correspond to an identification code, which is associated with a particular item of inventory. In one case, the memory 62 would contain a database of information concerning the inventory item corresponding to respective identification codes. Thus, when the controller 60, and particularly the barcode processor 142, determines the identification code from the barcode, it is appreciated that this data and information can be communicated to the memory 62 where a particular item can be accounted for and the information or data reflecting that accounting can be stored.

Further, the handheld computing device 10 is designed to function wirelessly. Some of the computing device's wireless functions will be subsequently discussed herein. Computing device 10 is designed to mount or seat within a cradle 32. Cradle 32 can be hardwired to a local area network (LAN) or other wider networks. This will permit data and information stored in the computing device to be downloaded and directed to one or more databases.

Turning to FIG. 6, there is shown therein a schematic illustration of the basic components of the computing device 10. Forming a part of the computing device 10 is a controller 60. Controller 60 comprises one or more microprocessors (See FIG. 11) that control the operation of the computing device 10 according to programs stored in a memory 62. This includes instructions that permit the user to navigate and control the functionality of the computing device 10. Memory 62 represents the entire hierarchy of memory used in such handheld electronic devices including RAM, flash memory, EPROM, EEPROM and other types of memory known and suitable for use in handheld electronic devices. Computer program instructions and data required for operation of the computing device 10 are stored in non-volatile memory such as those listed above. Memory 62 stores the various program instructions that permit controller 60 to control the operation of the computing device 10 and stores data and other information inputted into the computing device or fetched by the computing device during the course of its operation.

Continuing to refer to the schematic illustration of the computing device 10, the computing device includes an input (I/O) interface 64. I/O interface 64 lies generally between controller 60 and an array of components. Among the array of components is a user interface 66, embedded environmental sensors 80, wireless interface 100, wire interface 110, data capture module 120, expansion slot 17, and in some cases, embedded vital sign sensors 70.

User interface 66 comprises the alphanumeric keypad 24, stylus 20, rocker 18, touch screen 16, and in some cases, a vital signs input port 68. Vital signs input port 68 is designed to be connected to an array of instruments or devices that measure such vital signs as temperature, heart rate, and blood pressure. In one embodiment, the computing device 10 can be provided with embedded vital sign sensors 70. See FIG. 10. In this case, computing device 10 may include an embedded temperature sensor 70C, an embedded heart rate sensor 70B, and an embedded blood pressure sensor 70A. By being embedded in the computing device, these sensors are fully operable to sense and determine temperature, heart rate and blood pressure. An appropriate interface between the respective sensors 70A, 70B and 70C and the patient can be provided.

Turning to the embedded environmental sensors 80, in the case of the embodiment illustrated herein, there is a room temperature sensor 80A, a humidity sensor 80B, and a pressure or positive pressure sensor 80C. See FIG. 9. These sensors, while embedded within the computing device 10, are operative to sense, record and continuously store time correlated room temperatures, humidity's and pressures. Thus, the temperature, humidity and pressure in an operating room, for example, can be continuously sensed, determined and recorded during a surgical procedure. This will, of course, create a record of these environmental conditions that can be reviewed at any time and correlated with the time period that a patient occupied an operating table, for example, within an operating room.

Figure 7:
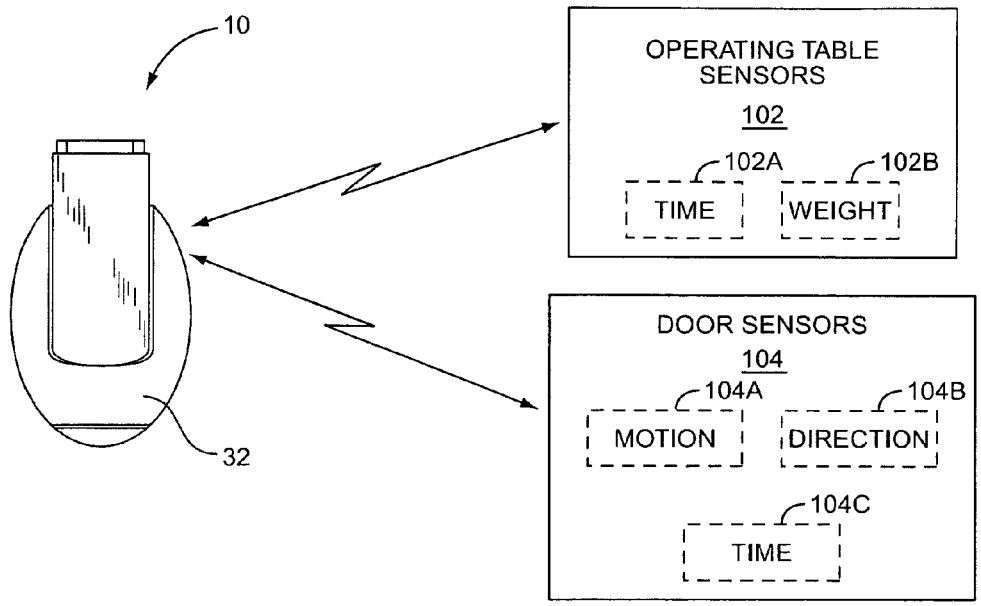
FIG. 7 is a schematic illustration showing the handheld computing device communicating with external sensors via a short-range radio interface.

Wireless interface 100 can be utilized as a means for inputting data and information into the computing device 10, or can be utilized for exporting data and information from the computing device 10. In some cases, wireless interface 100 can be utilized to monitor and record the status of certain elements in and around the operating room. Again, as with other components of the computing device, the recorded status of these elements is accomplished in real time and a time log can be generated from this data that indicates the status or condition of certain elements in and around an operating room, for example, over a period of time. In the way of an example, it may be desirable to record the time period that an operating table is occupied by a patient in an operating room during a surgical procedure. As indicated in FIG. 7, the wireless interface 100 can communicate with one or more operating table sensors 102. In the case of this example, the operating table sensors 102 would include a time sensor 102A and a weight sensor 102B. Coupled together, these two sensors will indicate the time that the patient first engaged the operating table and the time that the patient was removed from the operating table. This will, of course, indicate the total time that the patient occupied the operating table. The sensors utilized would be intelligent sensors. That is, the operating sensors 102 would have the ability to communicate to the computing device 10, via the wireless interface 100, information and data from which the controller 60 could determine when the operating table was occupied by a patient.

Similarly, the wireless interface 100 can be utilized to monitor and record the action of doors to the operating room. In this regard, as shown in FIG. 7, the operating room of a medical care facility would be provided with a number of door sensors 104. In this particular application, it may be desirable to sense and monitor the motion of a door, the direction of movement of the door, and the time frame in which a particular door was moved. Door sensors 104 would include a motion sensor 104A, a direction sensor 104B and a time sensor 104C. These three sensors combined, for example, will provide a record of the movement of a particular door to an operating room.

Figure 12:
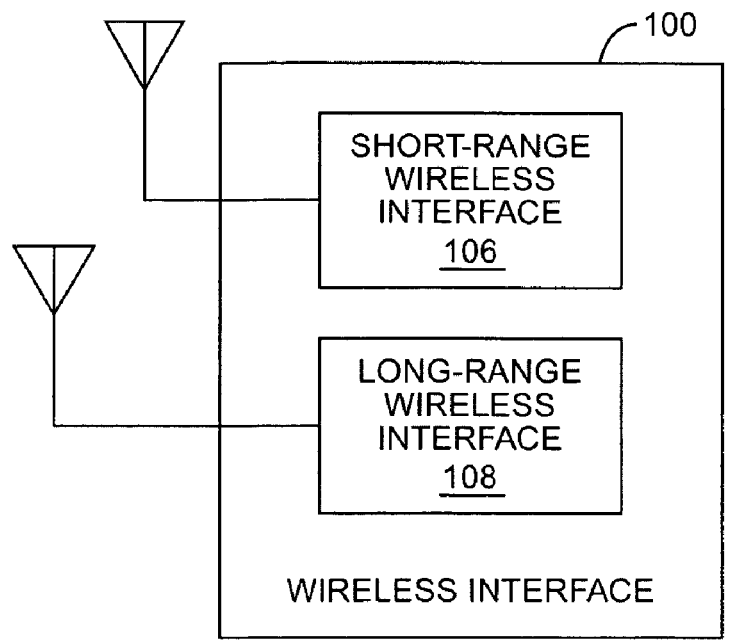
FIG. 12 is a schematic illustration of the wireless interface.
Figure 13:
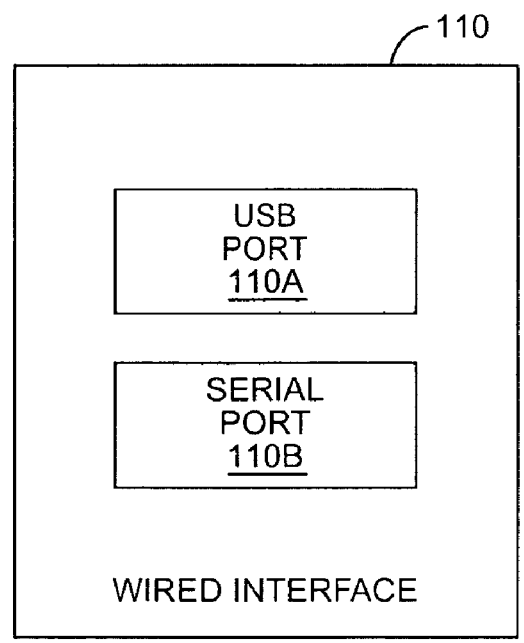
FIG. 13 is a schematic illustration of the wired interface.

Wireless interface 100 would include a short-range radio interface 106 and could include a long-range radio interface 108 (FIG. 12). In any event, the wireless interface 100 is typically coupled to an antenna for receiving and transmitting wireless signals. Wireless interface 100 preferably includes base band processing circuits that process signals transmitted and received by a transceiver. Alternatively, base band processing circuits may be incorporated into the system controller 60.

The short-range radio interface 106 would be particularly suited for sensing and transmitting data relating to the status of certain elements in and around an operating room. For example, the short-range radio interface 106 would be particularly suited for transmitting and receiving signals from the operating table sensors 102 and the door sensors 104. Accordingly, wireless interface 100 would include a short-range transceiver and a long-range wireless transceiver such as a cellular transceiver. The long-range wireless transceiver may be a fully functional cellular radio transceiver, which may operate according to any known standard, including standards known generally as the global system for mobile communications (GSM), TIA/EIA-136, etc. The short-range transceiver would be a short-range wireless transceiver such as a Bluetooth® transceiver, that enable wireless communications between two or more communication devices over short distances. As understood by those skilled in the art, Bluetooth® is a universal radio interface that enables two or more wireless devices to communicate wirelessly via short-range ad hoc networks. While one embodiment of the present invention may use a "Bluetooth® transceiver" and "Bluetooth® network" which refer to wireless communication over relatively short distances, i.e., less than 30 feet, those skilled in the art appreciate that the present invention is not limited to Bluetooth® systems and equipment, and that other short range systems, for example, infrared systems, are equally applicable.

Figure 8:
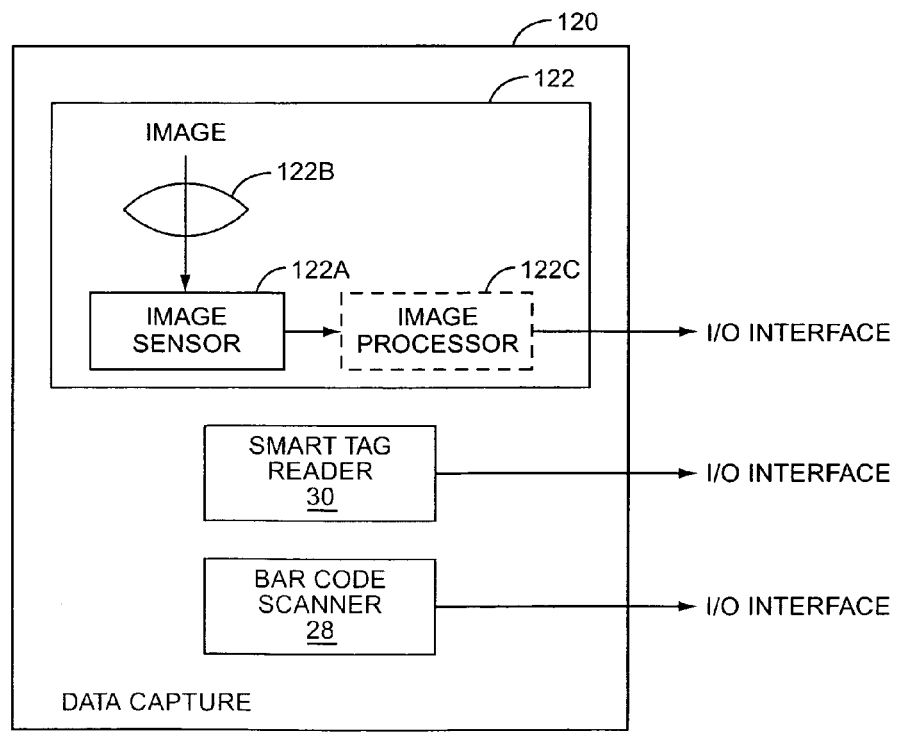
FIG. 8 is a detailed diagram of the data capture component illustrated in FIG. 6.

Handheld computing device 10 is provided with an embedded digital camera. Further, as discussed above, the computing device includes an RF tag reader 124 and a barcode reader/scanner 126. The digital camera, smartcode reader 124 and barcode reader 126 all form a part of the data capture module 120. See FIG. 6. Data capture module 120 includes the digital camera unit 122. Forming a part of the digital camera unit 122 is a digital camera and a lens 122B, an image sensor 122A and an image processor 122C. Lens 122B comprises a single lens or a plurality of lenses and collects and focused light onto the image sensor 122A. Image sensor 122A captures images formed by light collected and focuses by the lens 122B. Image sensor 122A may be any conventional image sensor such as a charge-coupled device (CCD) or a complimentary metal oxide semi-conductor (CMOS) image sensor. Image processor 122C can comprise a stand-alone processor as suggested in FIG. 8, or in the alternative, could be incorporated into the one or more processors that form the system controller 60. In any event, image processor 122C processes raw image data captured by image sensor 122A for subsequent storage in memory 62 or outputted to display 16. Image processor 122C may be a conventional digital signal processor programmed to process image data, which is well known in the art.

Further, handheld computing device 10 includes a number of other features that are useful in an operating room environment. Embedded within the handheld computing device 10 is a metal detector 150. Metal detector 150 is operative to detect metal objects such as surgical instruments that might be left internally within a patient after an operation. Hence, once the surgical procedure has been completed, and the incision areas closed, the handheld computing device 10 can be moved over the patient to scan for metal objects within the patient. Additionally the handheld computing device 10 includes a fluid temperature sensor 154. In surgical procedures, saline solutions are utilized to irrigate a wound or an open internal area of a patient. Typically, such saline solutions are removed from a warming cabinet and poured into a basin. From the basin the saline solution is transferred to the patient. The fluid temperature sensor 154 embedded within the handheld computing device can be utilized to sense and measure the temperature of the solution prior to the solution being transferred into the patient. Further, the handheld computing device 10 can be provided with a dosimeter 158. The dosimeter or dosimeter sensor 158 is operative to sense or read for radioopaque objects. In operating room environments, sponges, gauze, etc. are often provided with a radioopaque thread or tag. Thus, at the conclusion of a surgical procedure, the handheld computing device 10 can be moved over or rubbed over a patient's body to detect sponges, gauze, etc. that might have been inadvertently left within the patient.

Turning to the controller 60, as noted above, the controller includes a number of microprocessors. In the case of the handheld computing device 10 disclosed herein, the controller 60 would include a series of environmental processors. This would include a temperature processor 130, a humidity processor 132, and a pressure processor 134. Processors 130, 132, and 134 would be programmed to receive data from intelligent sensors 80A, 80B and 80C that yield data from which the various processors can determine temperature, humidity and pressure within the operating room. Further, the controller 60 would include a vital signs processor 136 for processing data relating to a patient's temperature, heart rate, and blood pressure. In addition, controller 60 would include any number of status processors that would process data relating to certain conditions in the operating room. For example, controller 60 would include a door processor 138 for processing data related to the status of one or more doors positioned around the operating room. In addition, an operating table processor 140 is provided that processes data received from the various intelligent sensors associated with the operating table. Further, the controller 60 would include a barcode processor 142 and a smart tag or RF tag processor 144. To work in conjunction with the metal detector 150, fluid temperature sensor 154 and dosimeter 158, the controller 60 includes a metal detector processor 152, a fluid temperature processor 156, and a dosimeter processor 160.

The handheld computing device 10 of the present invention has many applications in the medical care field. One of its principle uses is that of managing or controlling inventory in hospitals, and particularly managing and controlling inventory that is used by surgeons in operating rooms. When used as an inventory management and control tool, the present invention can be used to establish trends in usage and can even be utilized to generate unique pick lists for certain surgeons for a particular type of surgery.

When used as an inventory management tool the computing device 10 will accurately account for cost of supplies used in operating room procedures and will effectively contribute and allocate those costs to the patients that receive the benefit of the operating room supplies. In use, each item of inventory would include a unique identifier that identifies the particular item or supply. The unique identifier could be in the form of a barcode or an RF tag. Examples of the types of items utilized in operating rooms include basic sterile supplies, sometimes referred to as sterile bundles which include sterile gowns, gloves, bowls, etc.; trays of surgical instruments and disposable components thereof; disposable items such as staples, staplers, etc.; and implants. In addition, the use of certain instrumentation and disposable components associated therewith is for purposes of this disclosure considered an inventoried item for which the use thereof can be accounted for by utilizing unique identifiers on the instrumentation and disposable components thereof and utilizing the handheld computing device to track such usage.

During the course of a surgical procedure in an operating room, one or more individuals, nurses, attendants or other authorized personnel, would be designated to utilize the handheld computing device 10 to scan the unique identifiers associated with each of the items that are used in the course of the surgical procedure. It is appreciated that selected initial information should be entered into the handheld computing device such as the name of the patient, patient identifier number, operating room, identity of the one or more surgeons, etc. During the course of the surgical procedure, the computing device is placed in a scan mode, or the mode may be referred to as an inventory use and accounting mode. In any event, utilizing the smart tag reader 124 or barcode scanner 126, the unique identifiers associated with each item is scanned and the computing device, via the barcode processor 142 or smart tag processor 144, is able to count the identified items and enter data into the memory 62 of the device. Data entered identifies the used item, its cost and correlates that with a specific patient and any number of other information fields.

At certain time intervals, the data and information stored in the memory 62 of the computing device 10 is downloaded and directed to one or more central databases. Once such database would be an external database associated with the healthcare facility housing the operating room. This information and data pertaining to the supplies and items that were utilized in the course of a patient's surgery is thusly available for billing verification purposes. In addition to the database of the healthcare facility, the same data and information can be transmitted to other databases such as the database of the patient's insurance entity. Making detailed cost records available to insurance entities and HMOs should expedite the processing of insurance claims to the benefit of not only the patient, but also hospitals and healthcare providers in general.

In addition to cost accounting and inventory management and control in operating rooms and other areas of healthcare facilities, the handheld computing device 10 has many other uses, especially in the healthcare field. For example, it has applications in the telemedicine filed. Here the computing device 10 can be used remotely by patients to monitor, record and transmit to physicians vital sign information such as temperature, heart rate and blood pressure, and a host of other information that may be pertinent to all types of diseases and disorders. In this regard, the real time data stored in the memory 62 can be downloaded and transmitted via the Internet to a physician's website where the information is received and appropriately identified with a particular patient. Once in the physician's records, the information can be monitored and screened on a daily basis by a physician or his/her staff without requiring frequent office visits. Hence, the use of the handheld computing device 10 by patients has the potential to improve the quality of healthcare and reduce the cost of healthcare and to provide accurate and timely data and information to the attending physician.

Further, the handheld computing device 10 can be utilized by physicians, nurses, medical students and many others as an educational and resource tool. By providing Internet access or access to medical libraries and journals located in various networks, interested individuals can access medical literature from around the world. Furthermore, physicians can easily communicate with other physicians, recognized authorities in particular medical fields or physicians that have particular expertise treating certain diseases and abnormalities. This presents the medical community with the opportunity to widely disseminate effective treatment information and has the ability to substantially improve the level of healthcare that is available across the world, especially in underdeveloped regions that might not have the number of doctors per capita or the more experienced physicians found in more developed areas.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

The invention claimed is:

1. A handheld computing device for performing multiple applications in an operating room of a healthcare facility comprising:
   a. a processor;
   b. a memory;
   c. a display;
   d. one or more embedded environmental sensors for sensing, recording and storing in the memory environmental conditions within the operating room;
   e. an inventory management module for accounting for items used during the course of a surgery within the operating room; and
   f. the inventory management module including one or more scanners for reading identifiers associated with items used in the course of the surgery.

2. The handheld computing device of claim 1 wherein the scanner includes an RF tag reader for reading RF tags associated with items used in the surgery.

3. The handheld computing device of claim 1 wherein the scanner includes a barcode reader for reading barcodes associated with items used in the surgery.

4. The handheld computing device of claim 1 wherein the scanner includes both an RF tag reader and a barcode reader.

5. The handheld computing device of claim 1 including a digital camera for recording images within the operating room.

6. The handheld computing device of claim 1 wherein the one or more embedded environmental sensors are taken from the group consisting of a temperature sensor, humidity sensor, and pressure sensor.

7. The handheld computing device of claim 1 wherein the short-range radio interface communicates with one or more external intelligent sensors within the operating room.

8. The handheld computing device of claim 7 wherein the short-range radio interface communicates with an external intelligent sensor that measures the time a patient occupies an operating table within the operating room.

9. Then handheld computing device of claim 1 including a metal detector for detecting metal objects within a patient.

10. The handheld computing device of claim 1 including a dosimeter for detecting radioopaque objects within a patient's body.

11. The handheld computing device of claim 1 including a user interface.

12. The handheld computing device of claim 11 wherein the user interface comprises a keyboard.

13. The handheld computing device of claim 1 including a keyboard and wherein the keyboard is rotatively mounted and adapted to assume at least two different orientations.

14. A method of accounting for items used during a surgical procedure in an operating room of a medical facility, comprising:
  a. utilizing a handheld computing device in the operating room to account for items used during the course of a surgery performed in the operating room;
  b. utilizing the handheld computing device including:
    i. directing a signal from the handheld computing device towards an identifier that uniquely identifies an item to be used in the surgery;
    ii. reading the unique identifier and counting the item identified by the unique identifier;
    iii. storing the count in the handheld computing device and correlating the count with the item counted;
    iv. from time to time, downloading inventory accounting information from the handheld computer to an external database; and
  c. directing stored inventory accounting information from the handheld computing device to at least two databases including a healthcare facility database and a database of an insurance entity.

15. The method of claim 14 wherein the items identified and counted include sterile supplies, instruments and disposable components thereof, and disposable supplies.

16. The method of claim 14 further including directing the stored inventory accounting information from the handheld computing device to a central database via a LAN.

17. The method of claim 14 including directing the stored inventory accounting information from the handheld computing device wirelessly to a database.

18. A handheld computing device for performing multiple applications, comprising:
  a. a base;
  b. a flip pivotally connected to the base and rotatable back and forth with respect to the base;
  c. a keyboard;
  d. the handheld computing device including a processor, memory, and a display; and
  e. the keyboard rotatively mounted on the base, rotatable with respect to the flip, and rotatable between first and second positions separated by at least 90°;
  f. wherein the flip and keyboard are both simultaneously rotatable with respect to the base; and
  g. a transverse structure that forms at least a part of a pivot connection that pivotally connects the flip to the base, and an RF tag reader including a lens disposed in the transverse structure.

19. The handheld computing device of claim 18 further including a barcode reader incorporate in part at least in the transverse structure that forms a part of the pivot connection.

20. The handheld computing device of claim 18 wherein the flip includes a display and wherein the keyboard normally assumes an aligned position with the base and wherein the keyboard is rotatable with respect to the base such that the keyboard extends transversely across the base and overhangs opposite edges of the base.

21. The handheld computing device of claim 20 wherein the base includes a surrounding edge and wherein the keyboard is pivotable about a point on the base interiorally of the surrounding edge.

22. The handheld computing device of claim 20 wherein the flip includes a front and a back and wherein the display is disposed on the front of the flip; and where the base includes a front and a back wherein the keyboard is mounted on the front of the base; and wherein the flip is pivotably connected to the base such that the flip can pivot to an extreme open position where the back of the flip lies adjacent the back of the base.

23. The handheld computing device of claim 22 wherein in the extreme position the back of the flip abuts the back of the base.

24. The handheld computing device of claim 18 wherein the keyboard includes a pair of generally straight side edges and a pair of generally arcuately-shaped end edges.

25. A method of sensing and recording environmental conditions within an operating room of a medical care facility comprising: placing a handheld computing device within an operating room wherein the handheld computing device includes one or more embedded environmental sensors; sensing one or more environmental conditions within the operating room with the sensors embedded within the handheld computing device; and storing the sensed environmental conditions within a memory within the handheld computing device; the computing device communicating with a sensor associated with an operating table within the operating room, and sensing the presence of a patient on the operating table; and sensing and recording the time period that the patient occupies the operating table.

26. The method of claim 25 wherein the method entails sensing one or more environmental conditions taken from the group consisting of temperature, humidity and pressure.

27. The method of claim 25 including sensing temperature, humidity and pressure within the operating room via the embedded sensors within the handheld computing device.

28. The method of claim 25 further including utilizing the handheld computing device to sense the condition of one or more elements located remotely from the handheld computing device, but within the operating room.

29. The method of claim 25 including the computing device communicating with a sensor associated with an operating table within the operating room, and senses the presence 30. A method of accounting for items used during a surgical procedure in an operating room of a medical facility, comprising:
  a. utilizing a handheld computing device in the operating room to account for items used during the course of a surgery performed in the operating room;
  b. utilizing the handheld computing device including:
    i. directing a signal from the handheld computing device towards an identifier that uniquely identifies an item to be used in the surgery;
    ii. reading the unique identifier and counting the item identified by the unique identifier;

iii. storing the count in the handheld computing device and correlating the count with the item counted;

iv. from time to time, downloading inventory accounting information from the handheld computer to an external database; and c. sensing selected environmental conditions within the operating room with the handheld computing device including sensing and recording within the handheld computing device at least one of temperature, humidity, or pressure within the operating room.

31. A method of accounting for items used during a surgical procedure in an operating room of a medical facility, comprising:

a. utilizing a handheld computing device in the operating room to account for items used during the course of a surgery performed in the operating room;

b. utilizing the handheld computing device including:
   i. directing a signal from the handheld computing device towards an identifier that uniquely identifies an item to be used in the surgery;
   ii. reading the unique identifier and counting the item identified by the unique identifier;
   iii. storing the count in the handheld computing device and correlating the count with the item counted;
   iv. from time to time, downloading inventory accounting information from the handheld computer to an external database; and c. utilizing the handheld computing device to determine the time a patient occupied an operating table within the operating room during a surgical procedure.

32. A method of accounting for items used during a surgical procedure in an operating room of a medical facility, comprising:

a. utilizing a handheld computing device in the operating room to account for items used during the course of a surgery performed in the operating room;

b. utilizing the handheld computing device including:
   i. directing a signal from the handheld computing device towards an identifier that uniquely identifies an item to be used in the surgery;
   ii. reading the unique identifier and counting the item identified by the unique identifier;
   iii. storing the count in the handheld computing device and correlating the count with the item counted;
   iv. from time to time, downloading inventory accounting information from the handheld computer to an external database; and c. utilizing the handheld computing device to monitor one or more doors to the operating room and recording the number of times one or more doors to the operating room are opened during a surgical procedure.

33. The method of claim 32 including recording the time that the doors are opened during the course of the surgical prcedure.

* * * * *